(12) United States Patent  (10) Patent No.: US 7,673,992 B2
Wengler  (45) Date of Patent: Mar. 9, 2010

(54) DEVICE AND METHOD FOR DETERMINING THE AMERTOPIA OF AN OPTICAL SYSTEM

(75) Inventor: Peter Wengler, Erfurt (DE)

(73) Assignee: Carl Zeiss Meditec AG, Jena (DE)

( * ) Notice: Subject to any disclaimer, the term of this patent is extended or adjusted under 35 U.S.C. 154(b) by 405 days.

(21) Appl. No.: 10/562,501

(22) PCT Filed: Jun. 25, 2004

(86) PCT No.: PCT/EP2004/006918
§ 371 (c)(1),
(2), (4) Date: Mar. 3, 2008

(87) PCT Pub. No.: WO2005/000112
PCT Pub. Date: Jan. 6, 2005

(65) Prior Publication Data
US 2008/0192201 A1   Aug. 14, 2008

(30) Foreign Application Priority Data
Jun. 27, 2003  (DE) ................................ 103 29 165

(51) Int. Cl.
*A61B 3/02*  (2006.01)

(52) U.S. Cl. .................. 351/223; 351/229; 351/233; 351/246

(58) Field of Classification Search .................. 351/205, 351/212, 219, 227, 229, 239, 246, 247, 222, 351/223, 233, 3
See application file for complete search history.

(56) References Cited

U.S. PATENT DOCUMENTS

| 3,791,719 | A | 2/1974 | Kratzer et al. | 351/11 |
| 4,105,302 | A | 8/1978 | Tate, Jr. | 351/7 |
| 6,491,394 | B1 | 12/2002 | Blum et al. | 351/228 |
| 2002/0140902 | A1* | 10/2002 | Guirao et al. | 351/221 |
| 2003/0174281 | A1 | 9/2003 | Herekar et al. | 351/200 |

FOREIGN PATENT DOCUMENTS

WO   WO 97/43945   11/1997

* cited by examiner

*Primary Examiner*—Huy K Mai
(74) *Attorney, Agent, or Firm*—Darby & Darby

(57) ABSTRACT

A device and method for determining the defective vision of an optical system include a controllable optical element. The objective and subjective determination of the correction values are more greatly combined in that a measuring and controlling device forms a control loop with the controllable optical element, and the optical characteristics of the controllable element can be changed manually.

11 Claims, 2 Drawing Sheets

DEVICE AND METHOD FOR DETERMINING THE AMERTOPIA OF AN OPTICAL SYSTEM

The present invention relates to a device and a method for determining the ametropia of an optical system.

BACKGROUND

It is known to have the ametropia of the human eye determined subjectively by the patient, e.g. by lens arrangements placed upstream in the beam path of the eye. Myopia, hyperopia and astigmatism can, for example, be corrected by the doctor offering the patient lenses in a spectacles frame, the patient determining the correction of his ametropia subjectively with the help of a sight chart. Instead of suggesting different lenses by means of a trial frame, this can also take place by means of a phoropter. In order to shorten and simplify the method given the large number of parameters to be combined (sphere, cylinder, axis, binocular values, higher aberrations), it is customary to first carry out an objective measurement with an automatic refractometer or aberrometer, which is then subsequently subjectively confirmed or corrected. In general, this requires two steps which may mean a doctor and patient changing places.

A disadvantage of known devices and methods is that the objective determination of correction values and the subjective determination or correction of the objective measurement values takes place in different steps and sometimes also leads to significantly different results.

SUMMARY OF THE INVENTION

An object of the present invention is therefore to provide a device and a method with which the objective and subjective determinations of the correction values are more closely integrated.

A further or alternate object of the invention to provide a criterion by means of which a conclusion can already be drawn as to the degree of agreement with the subjective determination in the objective determination of the correction values.

The present invention provides a device for determining the ametropia of an optical system, comprising a controllable optical element which is operated by a measurement and control apparatus and the optical properties of which can be modified automatically and/or manually. The optical system can be the human eye itself, but it can also be a human eye which has been supplemented e.g. by means of a contact lens, at least one intraocular lens, spectacles, a combination of these elements or similar. The measurement and control apparatus preferably includes an automatic refractometer or aberrometer and an electronic circuit for controlling the controllable optical element. The controllable optical element can preferably be an electrically controllable phoropter, or else a lens or mirror system, e.g. an optometer and astigmometer. The controllable optical element and the measurement and control apparatus form a closed-loop control circuit which minimizes the remaining ametropia of the optical system. The optical system comprises a human eye and optionally also an artificial visual aid.

The controllable optical element can be a lens or mirror system, e.g. an optometer and astigmometer or an electrically controllable phoropter. It is also conceivable that the controllable optical element is an adaptively optical system, e.g. a controllable membrane mirror, microelement mirror, a controllable liquid lens or liquid-crystal lens. It is also conceivable within the framework of the invention to use a combination of different controllable optical elements. The measurement and control unit can comprise an automatic refractometer or aberrometer, this aberrometer being able to contain in particular a Shack-Hartman sensor, a Tscherning system, a Talbot interferometer, a Talbot-Moire interferometer, a confocal wave-front sensor or a point spread function sensor.

The controllable phoropter can contain phase plates. The latter can in particular have any defined spatially distributed phase displacement for light which is suitable to compensate even complex disturbances of the optical system to be examined. The complex disturbances can in particular contain higher-order aberrations which are described for example with the help of a wave front which represents the spatial distribution of the phase displacement or of the transit-time difference for the light.

The device for determining the ametropia of an optical system can also be designed such that dynamic processes, in particular those of the accommodation, are covered. For this purpose, fixation stimuli (optical test charts) are offered to the optical system which correspond to different distances or simulate the latter. Thus the fixation stimuli can be for example sight charts, statistical and/or dynamic images, 3-dimensional targets, binocular targets such as e.g. polatest, or special geometric patterns for the identification of individual aspects of the ametropia of the optical system. These different fixation stimuli can advantageously be produced with electronic displays such as liquid crystal, plasma, deformable mirror- or microdisplays. The latter can integrated in the device or also located outside the device (clear-view arrangement).

Furthermore, defined lighting conditions are possible in order to record the behaviour under different light conditions of the optical system to be examined. With such a device it is possible in particular to ascertain the ametropia for day and night vision. It is also advantageous to integrate a measuring system to record the pupil diameter under different lighting conditions of the optical system.

It is also possible according to the invention to determine the ametropia of the human eye binocularly. This can take place for example simultaneously, alternately or sequentially. It is advantageous to choose the binocular vergency angle to agree with the distance of the fixation target in order to create sight conditions that are as realistic as possible.

The invention also comprises the establishment of a criterion with which the expected deviation of a purely subjective compared with the objective ametropia determination is ascertained. According to the invention, a confidence value is preferably determined which can be derived from the accommodation behaviour of the optical system to be examined during the measurement and/or from the size of the higher-order aberrations absolutely or relative to the size of the lower orders. Thus for example, this value can be used to define an indicator which shows whether a further purely subjective determination of the ametropia of the optical system is also required.

A desired correction of the thus-ascertained ametropia is achieved according to the state of the art inter alia by spectacles of different complexity, such as e.g. purely spherical, aspherical, with cylinder and/or astigmatism correction or by correction of further higher orders. Further possibilities are the use of contact lenses or intraocular lenses and also various laser correction possibilities such as LASIK, LASEK, PRK, LTKP and the use of fs lasers. It is advantageous according to the invention with the controllable optical element during determination of the ametropia to correct the latter only to the extent permitted by the desired correction possibility. In a further development of the device according to the invention, it is provided that the beam path of a treatment laser or of a lighting system for diagnostic or therapeutic purposes is also reflected in the beam path of the device. This is of advantage in particular if the modifiable optical element is for example a contact lens, an intraocular lens or directly the cornea and/or the lens of the eye to be treated. In this case, the optical properties of the optical system are modified by the treatment laser by means of ablation or disruption respectively or by a lighting system using thermal or photochemical effects.

A device is also provided within the framework of the invention which is structured such that the ametropia of an optical system can be objectively recorded and/or compensated by means of at least one controllable optical element, at least one measurement and control apparatus, the device further containing means which allow a subjective modification of the ascertained values.

The present invention also provides a method for determining the ametropia of an optical system with a device comprising a controllable optical element and also a measurement and control apparatus, the controllable optical element being adjusted by the measurement and control apparatus in a first step such that the ametropia of the optical system is compensated. It is advantageous if in a further step the controllable optical element is adjusted manually by the patient to achieve a subjectively optimum compensation of the ametropia.

BRIEF DESCRIPTION OF THE DRAWINGS

Advantageous designs of the invention are explained in more detail in the drawings. There are shown in.

DETAILED DESCRIPTION

Figure 1:
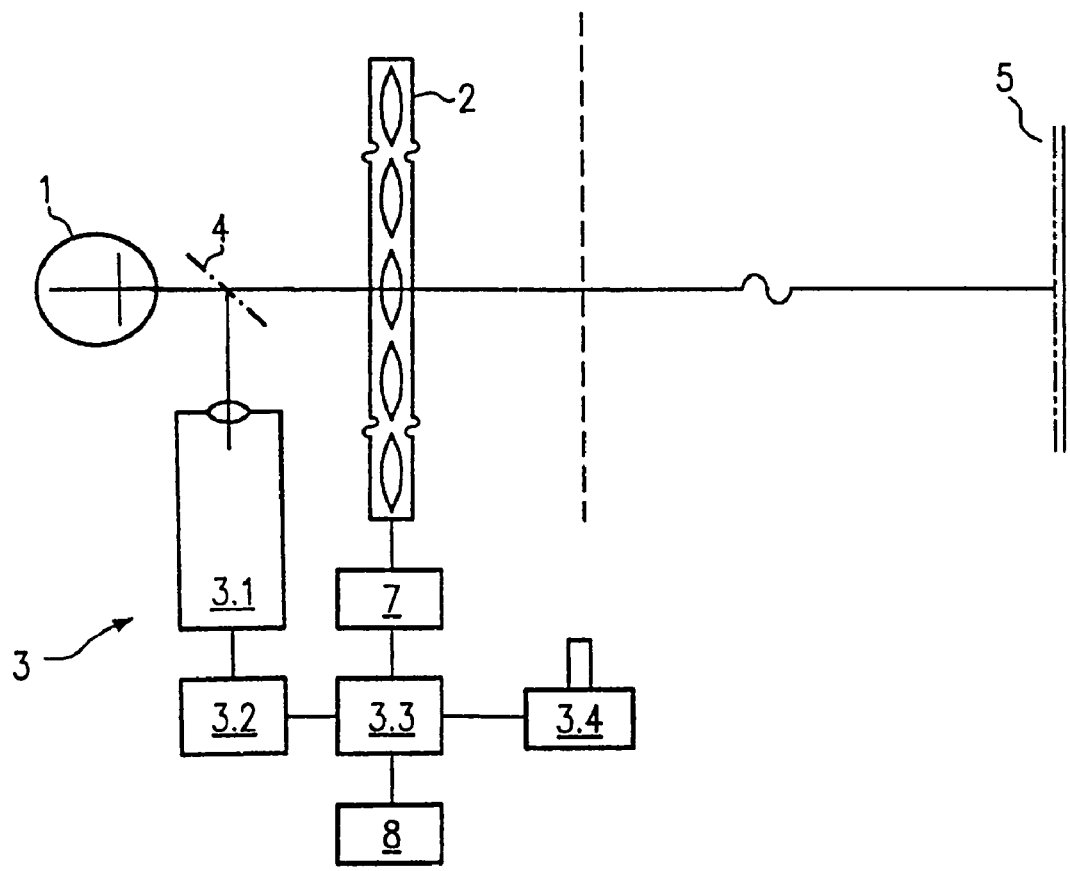
FIG. 1 an outline drawing of a first version of the device according to the invention.

Reference is made firstly to FIG. 1. An eye 1 of a patient looks through a controllable optical element 2 and through a beam splitter 4 onto an optical test chart 5. The human eye 1 to be examined can be equipped for example with additional visual aids such as a contact lens or similar and is therefore called optical system 1 in the remainder of the description. The controllable optical element 2 can for example be an electrically controlled phoropter. The beam path of a preferably automatic refractometer or aberrometer is reflected by means of the beam splitter 4. This is called measurement and control apparatus 3 hereafter. The measuring radiation of the measurement and control apparatus 3 and also the reflection of the beam splitter 4 lie expediently in the infrared region, with the result that a patient cannot recognize this radiation and is aware of only the optical test chart 5. The measurement and control apparatus 3 comprises an automatic refractometer or aberrometer 3.1 the measurement signals of which are processed via a processor 3.2 and a control apparatus 3.3 so that they control a drive 7 of the controllable optical element 2. Thus the ametropia of the optical system 1 is almost compensated. The control apparatus 3.3 can also be actuated via a manual control 3.4. A subjective subsequent correction can be carried out by the patient by means of the manual control 3.4 according to the seen optical test chart 5. The final correction values for a spectacles' prescription can be taken from a data output 8.

Figure 2:
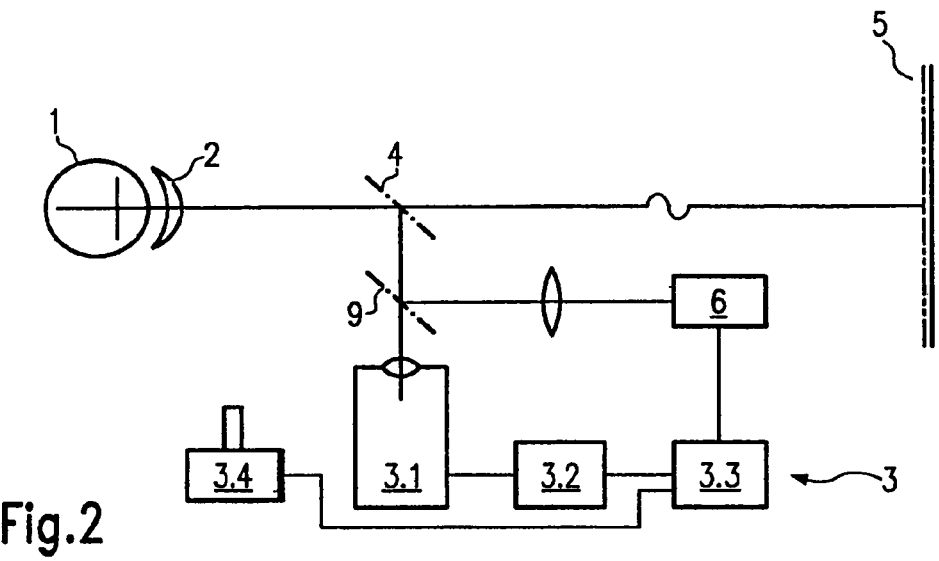
FIG. 2 an outline drawing of a second version of the device according to the invention.

FIG. 2 shows schematically an expanded version. The controllable optical element 2 is in this case a contact lens, intraocular lens or phase plate the refractive power of which is modified by material ablation by means of spatially and energetically controlled laser radiation until the ametropia of the patient's eye is objectively and subjectively compensated. For this purpose, the radiation of a laser 6 is reflected into the beam path by means of a second beam splitter 9. The structure and function of the closed-loop control circuit otherwise correspond to the version shown in FIG. 1.

Figure 3:
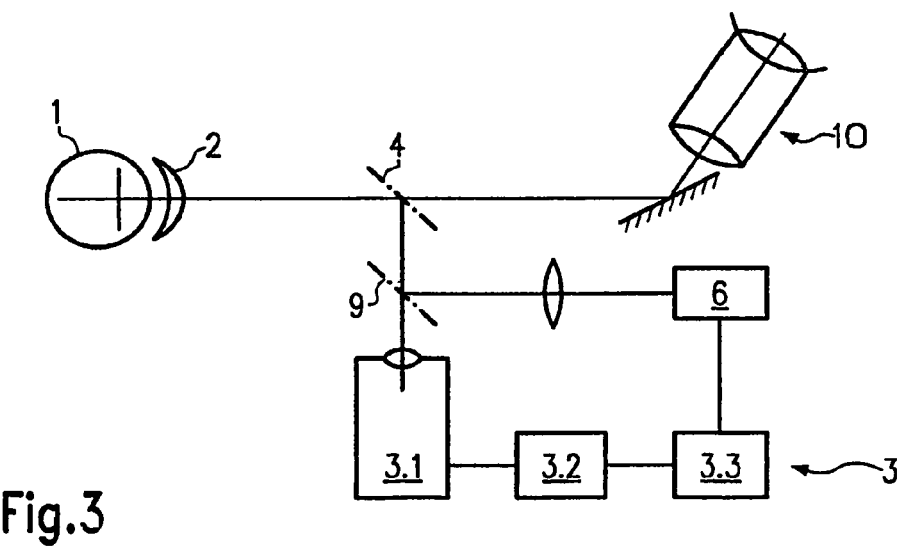
FIG. 3 an outline drawing of a third version of the device according to the invention.

FIG. 3 shows a third version of the device according to the invention in which, compared with the version shown in FIG. 2, the controllable optical element 2 is the patient's own cornea. Therefore, instead of an ablation of a contact lens by means of the laser 6, an immediate correction of the cornea is carried out according to the objectively measured correction values by means of known ablation procedures such as e.g. PRK, Lasik or Lasek. An immediate subjective monitoring of the visual capacity is not possible here, for which reason, instead of an optical test chart 5, an eye lens 10 is provided for observing the eye.

If the measuring beam path is reflected, seen in the direction of the eye, in front of the controllable optical element 2, the latter is measured together with the ametropic eye as a complete system. The return of the measurement and control signal to the modifiable or controllable optical element 2 results in a closed-loop control circuit which adjusts the signal to zero. Remaining image defects of the eye/correction-element system, for example image defects due to accommodation, are displayed and can be analyzed and taken into account as necessary. This also applies in the case of a corresponding optical-test-chart distance for prescribing reading spectacles. If the measuring system is reflected, seen in the direction of the eye, after the controllable optical element 2, only the optical system of the eye is measured, the signal remains and controls the controllable optical element 2 for the previously calculated compensation of the ametropia. It is not monitored by instruments, and only repercussions on the eye, such as accommodation, are displayed. In parallel with the regulation or control process for compensating the ametropia, the patient also has the option to modify the automatically set correction values manually until he senses optimally sharp or comfortable vision. This also applies, in particular with a phoropter, to the binocular compensation. This subjective correction gives the final values for dispensing spectacles or contact lenses.

The controllable optical element 2 can be a controllable phoropter or a lens or mirror system, e.g. an optometer and astigmometer. In conjunction with controllable material-processing lasers, e.g. an excimer laser, individually tailored corrections can also be carried out, for example by means of specially made spectacles lenses (phase plates) or contact lenses or direct ablation of the cornea, which may have resulted from a wave-front analysis. For processing, the laser is controlled on- or offline by the measurement system. For this purpose, the device according to FIG. 1 is provided with an additional reflection system according to FIG. 2. The effect of the corneal ablation can be tracked in real time physically and using instruments, but not subjectively by the patient in the current state of operating techniques.

What is claimed is:

1. A device for compensating an ametropia of an optical system, comprising:

a light source emitting a beam of light;

a controllable optical element having a plurality of optical properties receiving a first portion of the beam and being automatically adjustable to permit modification of at least one of a plurality of optical properties; and a measurement and control unit receiving at least a second portion of the beam and operatively connected to the controllable optical element and forming a closed-loop control circuit with the controllable optical element, the measurement and control system automatically adjusting the controllable optical element so as to compensate the ametropia of the optical system.

2. The device according to claim 1, wherein the optical system includes a human eye.

3. The device according to claim 2, wherein the optical system also includes an artificial visual aid.

4. The device according to claim 1, wherein the controllable optical element includes at least one of a controllable phoropter and an optometer with an astigmometer.

5. The device according to claim 4, wherein the controllable phoropter includes a plurality of phase plates.

6. The device according to claim 1, wherein the measurement and control unit includes at least one of an automatic refractometer and an aberrometer.

7. The device according to claim 1, further comprising a laser having a beam path and wherein the beam path is reflected into a beam path of the device.

8. The device as recited in claim 1, wherein the controllable optical element is configured to permit manual modification of at least one of the plurality of optical properties so as to achieve a subjectively optimum compensation of the ametropia.

9. A method for compensating an ametropia of an optical system, the method comprising:
    emitting light from a light source;
    passing at least a first portion of the light through a controllable optical element, the controllable optical element being automatically adjustable to permit modification of at least one of a plurality of optical properties of the controllable optical element;
    receiving at least a second portion of the light using a measurement and control unit, the measurement and control unit being operatively connected to the controllable optical element so as to form a closed-loop system;
    compensating the ametropia by adjusting the controllable optical element using the measurement and control unit.

10. The method as recited in claim 9, further comprising:
    further adjusting the controllable optical element manually so as to achieve a subjectively optimum compensation of the ametropia.

11. The method as recited in claim 10, wherein the optical system includes an eye of a patient and wherein the further adjusting is performed by the patient.

* * * * *